United States Patent [19]

Kondo et al.

[11] 4,292,038
[45] Sep. 29, 1981

[54] FORMAMIDE-CONTAINING LATEX AGGLUTINATING REAGENT FOR IMMUNOASSAY

[75] Inventors: Koichi Kondo, Osaka; Isamu Yoshida, Takatsuki; Takashi Kobayashi, Hikari, all of Japan

[73] Assignee: Takeda Chemical Industries, Ltd., Osaka, Japan

[21] Appl. No.: 116,465

[22] Filed: Jan. 29, 1980

[30] Foreign Application Priority Data

Jan. 31, 1979 [JP] Japan ................................. 54-10552
May 31, 1979 [JP] Japan ................................. 54-08504

[51] Int. Cl.³ ............................................. G01N 33/54
[52] U.S. Cl. .................................... 23/230 B; 252/408; 424/12
[58] Field of Search ........................ 424/12; 23/230 B; 252/408

[56] References Cited

U.S. PATENT DOCUMENTS 3,564,089 2/1971 Kiddy ................................ 424/12 X
4,046,723 9/1977 Dorman ............................ 424/12 X
4,088,749 5/1978 Grundman ............................. 424/12

OTHER PUBLICATIONS

"The Merck Index," Ninth Edition, M. Windholz et al., eds., pp. 431 and 1266, Merck & Co., Rahway, N.J., 1976.

Primary Examiner—Sidney Marantz
Attorney, Agent, or Firm—Wenderoth, Lind & Ponack

[57] ABSTRACT

By using a reagent for latex agglutination reaction which contains one or more members selected from the group consisting of a compound of the formula

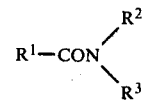

wherein $R^1$ is a hydrogen atom, a lower alkyl group or an amino group which may be substituted with a lower alkyl group and $R^2$ and $R^3$ are each a hydrogen atom or a lower alkyl group, and a di-lower alkyl sulfoxide, the non-specific agglutination can be remarkably prevented and thus greatly improving the reliability of the latex agglutination test results.

8 Claims, No Drawings

FORMAMIDE-CONTAINING LATEX AGGLUTINATING REAGENT FOR IMMUNOASSAY

The present invention relates to an improvement in latex agglutination reactions.

In recent years there have been increasingly and frequently employed clinical diagnostic methods using immunological procedures, because they are specific and have high sensitivity. Among them, a measurement utilizing the agglutination reaction of latex particles sensitized with an antigen or antibody has advantages that the procedures are simple and that the test results are obtained in a very short time. However, this method using the prior art latex diagnostic agents often misleads the diagnosis, because these agents are prone to cause non-specific agglutination reactions in the measurement of immunologically active substances contained in urine or body fluids such as serum, plasma, etc.

Under the above technical situation, the present inventors have unexpectedly found that the aforementioned non-specific agglutination can be prevented by conducting latex agglutination reactions in the presence of one or more members selected from the group consisting of a compound of the formula:

 (I)

wherein $R^1$ is a hydrogen atom, a lower alkyl group or an amino group which may be substituted with a lower alkyl group and $R^2$ and $R^3$ are each a hydrogen atom or a lower alkyl group and, a di-lower alkyl sulfoxide, and with further study, the present inventors have finally accomplished this invention.

Thus, the principal object of the present invention is to provide an excellent reagent for a latex agglutination reaction, which contains one or more members of the above-mentioned compounds. Another object is to provide an improved latex agglutination reaction with use of said reagent. Other objects will be made clear from the description and claims hereinafter.

In the formula (I), the lower alkyl group for $R^1$, $R^2$ and $R^3$ is preferably of up to 2 carbon atoms, and methyl is especially advantageous. The amino group for $R^1$ may be substituted with one or two lower alkyl groups which are preferably those of up to 2 carbon atoms, methyl being especially preferred. The lower alkyl group in the di-lower alkyl sulfoxide is preferably of up to 2 carbon atoms and methyl is most convenient. Representative examples of the compound of the formula (I) and the di-lower alkyl sulfoxide are urea, N-methylurea, N,N'-dimethylurea, N-methylformamide, N,N-dimethylformamide, N,N-diethylformamide, N-methylacetamide, N,N-dimethylacetamide, N,N-diethylacetamide, dimethyl sulfoxide, diethyl sulfoxide, etc. These compounds can be used alone or in combination. Especially, the combination of urea and N,N-dimethylformamide is most advantageous.

In the present invention, the above-mentioned non-specific agglutination can be prevented by conducting a latex agglutination reaction in the presence of one or more of the compounds (I) and di-lower alkyl sulfoxides (hereinafter referred to as the instant compound), thereby reducing false-positive results in the latex agglutination reaction, and thus remarkably increasing the reliability of the test. The instant compound is preferably present in the latex agglutination reaction system (after mixed with a test sample) at a concentration of about 1 to 13% (weight/volume)(hereinafter all the percent is expressed as weight/volume percent), especially about 1 to 7%.

The present invention can be applied to any reaction to detect immunologically active substances contained in the urine or body fluids (e.g. serum, plasma, etc.) of mammals, especially human, by using the agglutination with latex particles sensitized with an antigen or antibody corresponding to the substances. Representative examples of such immunologically active substances are serum proteins such as human immunoglobulin G, human immunoglobulin M, human immunoglobulin A, human albumin, human fibrinogen (fibrinogen, fibrin and their decomposed products), α-fetoprotein, C-reactive protein, $\beta_2$-microglobulin, myoglobin, etc.; hormones such as human chorionic gonadotropin (hereinafter referred to as HCG), human placental lactogen, insulin, steroids, etc.; immunoglobulin fractions, especially specific antibodies belonging to immunoglobulin G or immunoglobulin M (e.g. antiviral antibody, rheumatoid factor etc.), and the like.

In the present invention, the instant compound can be brought to be present in the latex agglutination reaction system by adding it to a diagnostic agent containing sensitized latex particles or by incorporating it in a diluent for a test sample. Accordingly, the expression "a reagent for latex agglutination reaction" is intended to comprehensively include the diagonostic agent (i.e. test reagent) containing the sensitized latex particles, the diluent for a test sample, and the like.

The latex particles which are sensitized with the antigen or antibody corresponding to the immunologically active substances may be of any latices which are employable for the latex agglutination test, and are exemplified by those of homopolymers and copolymers produced from styrene or its derivatives (e.g. methylstyrene, ethylstyrene, chlorostyrene etc.), olefins (e.g. ethylene, propylene etc.), acrylic acid or its esters (e.g. methyl acrylate, ethyl acrylate etc.), methacrylic acid or its derivatives (e.g. ethyl methacrylate, acrylonitrile, acrylamide etc.), dienes (e.g. butadiene, chloroprene, isoprene etc.), vinyl chloride, vinylidene chloride, vinyl acetate etc. Among them, the latices of the homopolymer or copolymer latices made of styrene, chlorostyrene, acrylic acid, vinyltoluene, methyl methacrylate etc. are advantageously used. These latices are preferably employed as those having a particle size of up to about 1μ, particularly of about 0.01 to 1.0μ, more particularly, about 0.1 to 0.6μ.

The treatment to sensitize the afore-mentioned latex particles with the antigen or antibody corresponding to the immunologically active substances can be effected by a known method in the art. The treating conditions vary to some degree depending on the physiochemical properties of the sensitizing substance and latex particles, and for example, where the latex particles are to be sensitized with an antibody, it is conveniently effected as follows. Antiserum is subjected to the salting out in a conventional manner to obtain γ-globulin fraction, which is then dissolved in a 0.005 to 0.2 M buffer of a pH of about 7 to 9 at a concentration of about 0.01 to 1%. As the buffer, glycine buffer, phosphate buffer, borate buffer and Good's buffers such as a buffer of N-2-hydroxyethylpiperadine-N'-2-ethanesulfonic acid (hereinafter referred to as HEPES) and N-tris(hydroxymethyl)methyl-2-aminoethanesulfonic acid (hereinafter referred to TES) are advantageously employed. A suspension of latex particles at a concentration of about 0.1 to 10% is added to the solution obtained above, which is then incubated at room temperature for about 1 to 6 hours or at about 37° C. to 60° C. for about 0.5 to 3 hours by allowing to stand or with stirring to sensitize the latex particles and the mixture is then centrifuged. The thus obtained sensitized latex particles are suspended again in a buffer to which the instant compound has already been added to give the reagent for the diagnosis. As the buffer, the afore-mentioned glycine buffer, phosphate buffer, borate buffer or Good's buffers such as HEPES and TES buffers having a pH of about 7 to 9 can be preferably employed. The preferred concentrations of the instant compound and the sensitized latex particles in the diagnostic agent in accordance with the present invention can be chosen from the range of about 2 to 52% and the range of about 0.4 to 1.4%, respectively, depending on whether a test sample is diluted or not before the latex agglutination reaction. More particularly, where the diagnosic agent is to be mixed with a test sample diluted with a conventional diluent, the diagnostic agent preferably contains the instant compound at a concentration about four times the aforementioned concentration range in the latex agglutination reaction system (about 1 to 13%, particularly about 1 to 7%) and the sensitized latex particles at about 0.9 to 1.4%. For the diagnostic agent which is to be directly mixed with a non-diluted test sample, the agent containing the instant compound at a concentration about two times the aforementioned concentration range (about 1 to 13%, particularly about 1 to 7%) and the sensitized latex particles at about 0.4 to 0.7% is preferably employed.

Where the instant compound is brought into a diluent for a test sample, any of the conventional buffers for diluting a test sample such as glycine buffer, borate buffer, phosphate buffer, Good's buffer e.g. HEPES and TES buffers, etc. can be employed as the fundamental component, and it may be suitably employed with a preferred pH range of about 6 to 9 and an electrolyte concentration of about 0.05 to 0.3 M. Especially, a 0.1 M glycine buffer (pH 8.2), a 0.1 M HEPES buffer (pH 7.5) etc. are advantageously employed. It is preferred that such buffer contains the instant compound at a concentration of about four times the aforementioned concentration range (about 1 to 13%, particularly about 1 to 7%).

If desired, the afore-mentioned reagents for the diagnosis can contain about 0.01 to 0.2% of serum albumin, preferably bovine serum albimun, and about 0.02 to 0.2% of a preservative such as sodium azide.

With use of the above-mentioned reagent, the latex agglutination reaction which comprises incubating a test sample and the sensitized latex particles to assess occurrence of the agglutination of the latex particles is conducted in the presence of the instant compound. The reaction may be carried out by a per se known technique such as the slide method described in e.g. Am. J. Clin. Pathol. 58, 305–316 (1972) and the test tube method described in e.g. Am. J. Obstet. Gynecol. 131, No. 6, 701–702 (1978).

The test sample such as urine, serum or plasma may be pretreated using an appropriate filter or may be directly subjected to the reaction without filtration.

By the present invention, the non-specific agglutination in the latex agglutination reaction can be remarkably prevented and thus greatly improving the reliability of the test results.

The effect of the present invention will be further illustrated in the following Examples and Test Examples which are not intended to restrict the scope of the present invention.

Throughout the present specification as well as in claims, the abbreviations "mg", "g", "μl", "ml", "μ", "°C.", "M", "N" and "r.p.m." respectively refer to "milligram(s)", "gram(s)", "microliter(s)", "milliliter(s)", "micron(s)", "degree(s) centigrade", "molar concentration", "normality" and "revolution(s) per minutes", and percentages are weight/volume unless otherwise specified.

EXAMPLE 1

| Glycine | 3.75 g |
| --- | --- |
| Urea | 60 g |
| Sodium azide | 0.5 g |

The above ingredients were dissolved in 400 ml of distilled water and the pH was adjusted to 8.2 by adding 1 N NaOH, after which distilled water was added to make the total volume 500 ml to give a diluent for a test sample.

EXAMPLE 2

| HEPES | 11.9 g |
| --- | --- |
| N,N-Dimethylformamide | 100 g |
| Sodium azide | 0.5 g |

The above ingredients were dissolved in 400 ml of distilled water and the pH was adjusted to 7.5 by adding 1 N NaOH, after which distilled water was added to make the total volume 500 ml to give a diluent for a test sample.

EXAMPLE 3

| Glycine | 7.5 g |
| --- | --- |
| N,N-Dimethylformamide | 75 g |
| Sodium azide | 0.5 g |

The above ingredients were dissolved in 400 ml of distilled water and the pH was adjusted to 8.6 by adding 1 N NaOH, after which distilled water was added to make the total volume 500 ml to give a diluent for a test sample.

EXAMPLE 4

| HEPES | 5.95 g |
| --- | --- |
| Dimethyl sulfoxide | 100 g |
| Sodium azide | 0.5 g |

The above ingredients were dissolved in 400 ml of distilled water and the pH was adjusted to 7.2 by adding 1 N NaOH, after which distilled water was added to make the total volume 500 ml to give a diluent for a test sample.

EXAMPLE 5

| | |
|---|---|
| HEPES | 11.9 g |
| Urea | 50 g |
| N-N-Dimethylformamide | 50 g |
| Sodium azide | 0.5 g |

The above ingredients were dissolved in 400 ml of distilled water and the pH was adjusted to 7.5 by adding 1 N NaOH, after which distilled water was added to make the total volume 500 ml to give a diluent for a test sample.

EXAMPLE 6

| | |
|---|---|
| Glycine | 3.75 g |
| N,N-Diethylformamide | 50 g |
| Sodium azide | 0.5 g |

The above ingredients were dissolved in 400 ml of distilled water and the pH was adjusted to 8.0 by adding 1 N NaOH, after which distilled water was added to make the total volume 500 ml to give a diluent for a test sample.

EXAMPLE 7

| | |
|---|---|
| Glycine | 7.5 g |
| N,N-Diethylacetamide | 50 g |
| Sodium azide | 0.5 g |

The above ingredients were dissolved in 400 ml of distilled water and the pH was adjusted to 7.8 by adding 1 N NaOH, after which distilled water was added to make the total volume 500 ml to give a diluent for a test sample.

EXAMPLE 8

| | |
|---|---|
| HEPES | 11.9 g |
| Diethyl sulfoxide | 30 g |
| Sodium azide | 0.5 g |

The above ingredients were dissolved in 400 ml of distilled water and the pH was adjusted to 7.5 by adding 1 N NaOH, after which distilled water was added to make the total volume 500 ml to give a diluent for a test sample.

EXAMPLE 9

| | |
|---|---|
| HEPES | 11.9 g |
| N-Methylurea | 75 g |
| Sodium azide | 0.5 g |

The above ingredients were dissolved in 400 ml of distilled water and the pH was adjusted to 8.2 by adding 1 N NaOH, after which distilled water was added to make the total volume 500 ml to give a diluent for a test sample.

EXAMPLE 10

| | |
|---|---|
| Glycine | 3.75 g |
| N-Methylformamide | 100 g |
| Sodium azide | 0.5 g |

The above ingredients were dissolved in 400 ml of distilled water and the pH was adjusted to 8.6 by adding 1 N NaOH, after which distilled water was added to make the total volume 500 ml to give a diluent for a test sample.

EXAMPLE 11

| | |
|---|---|
| Glycine | 3.75 g |
| N-Methylacetamide | 75 g |
| Sodium azide | 0.5 g |

The above ingredients were dissolved in 400 ml of distilled water and the pH was adjusted to 8.6 by adding 1 N NaOH, after which distilled water was added to make the total volume 500 ml to give a diluent for a test sample.

EXAMPLE 12

| | |
|---|---|
| HEPES | 11.9 g |
| Urea | 60 g |
| N,N-Dimethylformamide | 50 g |
| Sodium azide | 0.5 g |

The above ingredients were dissolved in 400 ml of distilled water and the pH was adjusted to 7.5 by adding 1 N NaOH, after which distilled water was added to make the total volume 500 ml to give a diluent for a test sample.

EXAMPLE 13

(1) Anti-C-reactive protein serum obtained by immunizing rabbits was subjected to the salting out using ammonium sulfate in a conventional manner to obtain γ-globulin fraction, which, after the dialysis, was dissolved in a 0.01 M phosphate buffer of pH 8.2 to obtain a 0.2% γ-globulin solution. To 10 ml of this solution was added an equal volume of a 2% polystyrene latex dispersion (particle size 0.2μ; dispersed with a 0.01 M phosphate buffer of pH 8.2) and the latex particles were sensitized at 37° C. for 2 hours with occasional shaking. The centrifugal separation at 12,000 r.p.m. for 15 minutes gave the latex particles sensitized with anti-C-reactive protein antibody as the precipitate.

| (2) | |
|---|---|
| Glycine | 3.75 g |
| Urea | 30 g |
| N,N-Dimethylacetamide | 25 g |
| Bovine serum albumin | 0.25 g |
| Sodium azide | 0.25 g |

The above ingredients were dissolved in 400 ml of distilled water and the pH was adjusted to 8.2 by adding 1 N NaOH, after which distilled water was added to make the total volume 500 ml to obtain a solution, in which the sensitized latex particles prepared in (1) above were dispersed at a concentration of 0.6% to give a diagnostic agent for measuring C-reactive protein, containing anti-C-reactive protein antibody sensitized latex. This agent can be provided for the agglutination reaction without diluting a test sample.

EXAMPLE 14

(1) Anti-human fibrinogen serum obtained by immunizing rabbits was subjected to the salting out using ammonium sulfate in a conventional manner to obtain γ-globulin fraction, which, after the dialysis, was dissolved in a 0.01 M phosphate buffer of pH 8.0 to obtain a 0.2% γ-globulin solution. To 10 ml of this solution was added an equal volume of a 2% polystyrene latex dispersion (particle size 0.25μ; dispersed with a 0.01 M phosphate buffer of pH 8.2) and the latex particles were sensitized at room temperature for 6 hours with occasional shaking. The centrifugal separation at 10,000 r.p.m. for 15 minutes gave the latex particles sensitized with anti-human fibrinogen antibody as the precipitate.

| (2) | |
|---|---|
| HEPES | 5.95 g |
| Urea | 25 g |
| N,N-Dimethylformamide | 25 g |
| Bovine serum albumin | 0.25 g |
| Sodium azide | 0.25 g |

The above ingredients were dissolved in 400 ml of distilled water and the pH was adjusted to 7.5 by adding 1 N NaOH, after which distilled water was added to make the total volume 500 ml to give a solution, in which the sensitized latex particles prepared in (1) above were dispersed at a concentration of 0.6% to give a diagnostic agent for measuring fibrinogen, fibrin and their decomposition products. This agent can be provided for the agglutination reaction without diluting a test sample.

| | |
|---|---|
| Glycine | 3.75 g |
| N,N-Dimethylformamide | 10 g |
| Sodium azide | 0.5 g |

The above ingredients were dissolved in 400 ml of distilled water and the pH was adjusted to 7.5 by adding 1 N NaOH, after which distilled water was added to make the total volume 500 ml to give a solution, in which the sensitized latex particles prepared in Example 13 (1) were dispersed at a concentration of 0.6% to give a diagnostic agent for measuring C-reactive protein. This agent can be provided for the agglutination reaction without diluting a test sample.

EXAMPLE 16

(1) Human γ-globulin (Cohn's fraction II) was dissolved in a 0.01 M phosphate buffer of pH 8.0 at a concentration of 0.3%. To 10 ml of the thus obtained solution was added an equal volume of a 2% polystyrene latex dispersion (particle size 0.15μ; dispersed with a 0.01 M phosphate buffer of pH 8.0) and the latex particles were sensitized at 56° C. for 2 hours with occasional shaking. The centrifugal separation at 15,000 r.p.m. for 30 minutes gave human γ-globulin sensitized latex particles for detecting rheumatoid factor as the precipitate.

| (2) | |
|---|---|
| Glycine | 3.75 g |
| N,N-Dimethylformamide | 30 g |
| Bovine serum albumin | 0.25 g |

-continued

| (2) | |
|---|---|
| Sodium azide | 0.25 g |

The above ingredients were dissolved in 400 ml of distilled water and the pH was adjusted to 8.0 by adding 1 N NaOH, after which distilled water was added to make the total volume 500 ml to give a solution, in which the sensitized latex particles prepared in (1) above were dispersed at a concentration of 0.6% to give a diagnostic agent for detecting rheumatoid factor. This agent can be provided for the agglutination reaction without diluting a test sample.

EXAMPLE 17

(1) Two mg of HCG (5000 IU/mg) were dissolved in 1 ml of saline, mixed with 1 ml of Freund's complete adjuvant and used to immunize rabbits at three-week intervals 4 times to obtain anti-HCG serum. The thus obtained antiserum was salted out using ammonium sulfate in a conventional manner to obtain γ-globulin fraction which was then, after the dialysis, dissolved in a 0.01 M phosphate buffer of pH 8.2 to obtain a 0.2% γ-globulin solution. To 10 ml of the γ-globulin solution thus obtained was added an equal volume of a 2% polystyrene latex dispersion (particle size 0.3μ; dispersed with a 0.01 M phosphate buffer of pH 8.2) and the latex particles were sensitized at 37° C. for 2 hours with occasional shaking. The centrifugal separation at 9000 r.p.m. for 15 minutes gave latex particles sensitized with anti-HCG antibody as the precipitate.

| (2) | |
|---|---|
| Glycine | 3.75 g |
| Urea | 75 g |
| N,N-Dimethylacetamide | 50 g |
| Bovine serum albumin | 0.5 g |
| Sodium azide | 0.5 g |

The above ingredients were dissolved in 400 ml of distilled water and the pH was adjusted to 8.2 by adding 1 N NaOH, after which distilled water was added to make the total volume 500 ml to give a solution, in which the anti-HCG antibody sensitized latex particles prepared in (1) above were dispersed at a concentration of 1% to give a diagnostic agent containing anti-HCG antibody sensitized latex for checking pregnancy. For use, this agent is mixed with a test sample diluted with a conventional diluent.

EXAMPLE 18

| | |
|---|---|
| HEPES | 5.95 g |
| Urea | 30 g |
| N,N-Dimethylformamide | 25 g |
| Bovine serum albumin | 0.25 g |
| Sodium azide | 0.25 g |

The above ingredients were dissolved in 400 ml of distilled water and the pH was adjusted to 7.5 by adding 1 N NaOH, after which distilled water was added to make the total volume 500 ml to give a solution, in which the anti-HCG antibody sensitized latex particles prepared in Example 17 (1) were dispersed at a concentration of 0.6% to give a diagnonostic agent for checking pregnancy. This product can be provided for the agglutination reaction without diluting a test sample.

Test Example 1

The anti-C-reactive protein antibody sensitized latex particles obtained in Example 13 (1) were dispersed in a 0.1 M glycine buffer (pH 8.2) containing 0.1% of bovine serum albumin and 0.1% of sodium azide to give a 1.2% dispersion. About 50 μl of a human serum sample to be tested were dropped onto a cleaned glass plate and, there was added about 25 μl of each of the diluents described in Examples 1 to 5 and, as the controls, a 0.1 M glycine buffer of pH 8.2 and containing 0.1% of sodium azide (hereinafter referred to as Diluent G) and a 0.1 M HEPES buffer of pH 7.5 and containing 0.1% of sodium azide (hereinafter referred to as Diluent H) to the glass plate, followed by the addition of 25 μl of the above sensitized latex suspension and shaking for 3 minutes, after which the mixture was examined for the occurrence of the agglutination. Also in a system which did not utilize a diluent for a test sample, about 50 μl of the diagnostic agent for measuring C-reactive protein obtained in Example 13 (2) were added to about 50 μl of a serum sample and shaken. After three minutes, the mixture was observed for the occurrence of the agglutination. The results are shown in Table 1.

TABLE 1

| Measuring System | Detection of C-Reactive Protein Sample No. | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Diluent for Test Sample: | | | | | | | | | | | | |
| Diluent G | + | + | + | + | + | + | + | − | ± | + | − | − |
| Diluent H | + | + | + | + | + | + | + | − | ± | ± | − | − |
| Example 1 | + | + | + | + | + | ± | + | − | − | − | − | − |
| Example 2 | + | + | + | + | + | + | + | − | − | − | − | − |
| Example 3 | + | + | + | + | + | ± | + | − | − | − | − | − |
| Example 4 | + | + | + | + | + | ± | + | − | − | − | − | − |
| Example 5 | + | + | + | + | + | ± | + | − | − | − | − | − |
| Example 13 (2) | + | + | + | + | + | ± | + | − | − | − | − | − |
| Capillary Method | + | + | + | + | ± | ± | + | − | − | − | − | − |

+: positive;
±: doubtful-positive;
−: negative.
(The same shall apply hereinafter)

As evident from the results in Table 1, when there was no urea, N,N-dimethylformamide, N,N-dimethylacetamide or dimethyl sulfoxide present in the diluent for a test sample or the latex dispersion, more false-positive cases were observed as compared with the diagnostic results by the conventional capillary sedimentation method. On the other hand, in the systems using the diluents of Examples 1 to 5 and the diagnostic agent for measuring C-reactive protein obtained in Example 13 (2) respectively, the results showed good agreement with those obtained by the capillary sedimentation method.

Test Example 2

About 50 μl of a human serum sample were dropped onto a cleaned glass plate and about 50 μl of the anti-human fibrinogen antibody sensitized latex particle dispersion obtained in Example 14 (2) were added, after which the mixture was shaken for 2 minutes and then examined for the occurrence of the agglutination. Separately, as the control, the sensitized latex particles in the form of a precipitate obtained in Example 14 (1) were dispersed in a 0.05 M HEPES buffer of pH 7.5 containing 0.05% of bovine serum albumin and 0.05% of sodium azide at a concentration of 0.6% to obtain a suspension of anti-human fibrinogen antibody sensitized latex particles, and similarly tested for comparison. The results shown in Table 2 were obtained.

TABLE 2

| Diagnostic Agent Used | Detection of Fibrin and Fibrinogen Decomposition Products Sample No. | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Example 14 (2) | − | + | + | − | − | − | + | − | ± | + | − | + |
| Control | − | + | + | + | − | − | + | + | + | + | − | + |

As shown in Table 2, there are two cases fallen in different results (i.e. Sample Nos. 4 and 8). Since these samples were not absorbed even by treating with anti-human fibrinogen antibody, it was judged that the results obtained using the control falsely showed positive.

Test Example 3

About 50 μl of a human serum sample were dropped onto a cleaned glass plate and about 50 μl of the human γ-globulin sensitized latex particle dispersion obtained in Example 16 (2) were added, after which the mixture was shaken for 2 minutes and then examined for the occurrence of the agglutination. Separately, as the control, the sensitized latex particles in the form of a precipitate obtained in Example 16 (1) were dispersed in a 0.1 M glycine buffer of pH 8.0 containing 0.05% of bovine serum albumin and 0.05% of sodium azide at a concentration of 0.6% to obtain a suspension of human γ-globulin sensitized latex particles and used for comparison. The results shown in Table 3 were obtained.

TABLE 3

| Diagnostic Agent Used | Detection of Rheumatoid Factor Sample No. | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Example 16 (2) | + | + | + | − | − | ± | + | − | − | + | − | + |
| Control | + | + | + | − | + | + | + | − | + | + | − | + |

As shown in Table 3, there are two cases fallen in different results (Sample Nos. 5 and 9). When these samples were tested by avoiding the influence of the serum components by the 20-fold dilution method using a conventional diluent, both cases showed the same results, negative. Thus, use of the diagnostic agent of this invention makes it possible to measure rheumtoid factor without diluting the serum sample.

Test Example 4

The anti-HCG antibody sensitized latex particles obtained in Example 17 (1) were dispersed in a 0.1 M glycine buffer of pH 8.2 at a concentration of 1%. As the urine to be tested, 10 urine samples which showed a tendency to cause the non-specific agglutination were taken from non-pregnant women. As the diluent for a test sample, each of the diluents of Examples 1 to 5 was used, and as the controls, the afore-mentioned Diluents G and H were used. Two drops of the urine sample were dropped onto a cleaned glass plate and one drop of each diluent was added and mixed, after which one drop of the afore-mentioned anti-HCG antibody sensitized latex suspension was added thereto and shaken for 3 minutes. The results of the examination for the occurrence of the agglutination are shown in Table 4 appearing later.

As is clear from the table, when the diluent for a test sample did not contain urea, N,N-dimethylformamide, N,N-dimethylacetamide or dimethyl sulfoxide, i.e., in both the cases of Diluents G and H, the proportions that the test indicated pregnancy were 10 out of 10 including the doubtful-positive cases. This is due to the non-specific agglutination reaction, although the samples were taken from non-pregnant women.

On the other hand, where the diluents prepared in Examples 1 to 5 were used, all the cases showed negative reactions, thus indicating no wrong diagnosis.

Next, using each of the diluents of Examples 1 to 5, the sensitivity of the latex agglutination reaction was tested on the standard solutions having varying levels of 0.5 to 5,000 IU/ml and urine samples at the initial stage of pregnancy each containing a low level of HCG (about 1 IU/ml). The results are shown in Table 5 appearing later.

Test Example 5

According to the procedures described in Test Example 4 and using the diluents of Example 1, 2 and 5 and, as the controls, Diluents G and H, respectively, the latex agglutination reaction for diagnosing pregnancy was conducted on urine samples of 200 non-pregnant women cases.

As shown in Table 6 appearing later, there were 6 positive cases and 20 doubtful-positive cases with Diluent G and 7 positive cases and 15 doubtful-positive cases with Diluent H, whereas all the cases showed negative when the diluents of Examples 1, 2 and 5 were used.

Test Example 6

According to the procedures described in Test Example 4 and using each of the diluents of Examples 1, 2 and 5 as the diluents for test samples, the latex agglutination reaction for diagnosing pregnancy was conducted on urine samples of 200 women definitely diagnosed as pregnant by clinical diagnoses. With each diluent, all the cases showed positive results just in aggreement with the clinical diagnoses.

Test Example 7

According to the procedures described in Test Example 4 and using the diluents of Examples 1, 2 and 5 respectively as the diluents for test samples, the latex agglutination reaction was conducted on each urine sample of 50 non-pregnant women and 50 women positively diagnosed as pregnant. With each diluent, all the urine samples of the non-pregnant women showed negative and all the urine samples of the pregnant women showed positive.

TABLE 4

Comparison of Diluents for Test Samples Tested on Urine Samples of Non-pregnant Women

| Diluent for Test Sample | \multicolumn{10}{c}{Sample No.} | | | | | | | | | |
|---|---|---|---|---|---|---|---|---|---|---|
| | 1 | 2 | 3 | 4 | 5 | 6 | 7 | 8 | 9 | 10 |
| Diluent G | ± | ± | ± | + | ± | + | ± | ± | + | + |
| Diluent H | + | ± | ± | + | ± | + | + | ± | + | + |
| Example 1 | − | − | − | − | − | − | − | − | − | − |
| Example 2 | − | − | − | − | − | − | − | − | − | − |
| Example 3 | − | − | − | − | − | − | − | − | − | − |
| Example 4 | − | − | − | − | − | − | − | − | − | − |

TABLE 4-continued

Comparison of Diluents for Test Samples Tested on Urine Samples of Non-pregnant Women

| Diluent for Test Sample | \multicolumn{10}{c}{Sample No.} | | | | | | | | | |
|---|---|---|---|---|---|---|---|---|---|---|
| | 1 | 2 | 3 | 4 | 5 | 6 | 7 | 8 | 9 | 10 |
| Example 5 | − | − | − | − | − | − | − | − | − | − |

TABLE 5

Comparison of Diluent for Test Samples Tested on Standard HCG Solutions and Urine Samples at the Initial Stage of Pregnancy

| Test Sample | | Dil. G | Dil. H | Ex. 1 | Ex. 2 | Ex. 3 | Ex. 4 | Ex. 5 |
|---|---|---|---|---|---|---|---|---|
| Standard HCG (IU/ml) | 0.0 | − | − | − | − | − | − | − |
| | 0.5 | ± | ± | ± | ± | ± | ± | ± |
| | 1 | + | + | + | + | + | + | + |
| | 2 | + | + | + | + | + | + | + |
| | 3 | + | + | + | + | + | + | + |
| | 2,000 | + | + | + | + | + | + | + |
| | 3,000 | + | + | + | + | + | + | + |
| | 5,000 | + | + | + | + | + | + | + |
| Urine Samples at the Initial Stage of Pregnancy (ca. 1 IU/ml) | A | + | + | + | + | + | + | + |
| | B | + | + | + | + | + | + | + |
| | C | + | + | + | + | + | + | + |
| | D | + | + | + | + | + | + | + |
| | E | + | + | + | + | + | + | + |

TABLE 6

Comparison of Diluent for Test Samples Tested on Urine Samples of 200 Non-pregnant Women

| Diluent for Test Sample | Test Results (Numbers of Cases) | | |
|---|---|---|---|
| | Positive | Doubtful-Positive | Negative |
| Diluent G | 6 | 20 | 174 |
| Diluent H | 7 | 15 | 178 |
| Example 1 | 0 | 0 | 200 |
| Example 2 | 0 | 0 | 200 |
| Example 5 | 0 | 0 | 200 |

TEST EXAMPLE 8

The anti-HCG antibody sensitized latex particles obtained in Example 17 (1) were dispersed in a 0.05 M borate buffer of pH 7.5 and containing 0.1% of sodium azide at a concentration of 1% to obtain a diagnostic agent for the latex agglutination reaction for checking pregnancy. Using the urine samples as mentioned in Test Example 4 and the diluent for test samples of Examples 1 to 5 respectively, the latex agglutination was conducted by adding 1 drop (about 25 μl) of each diluent to 2 drops (about 50 μl) of each urine sample and mixing, followed by the addition of 1 drop (about 25 μl) of the diagnostic agent obtained above to assess the effects of the diluents.

The results are shown in Table 7 below, from which it is seen that when the diluent for a test sample did not contain urea, N,N-dimethylformamide, N,N-dimethylacetamide or dimethyl sulfoxide, i.e., in the case of Diluents G and H, the proportions that the tests indicated pregnancy were 10 out of 10 including doubtful-positive cases with both diluents due to the non-specific agglutination reaction though the samples were taken from non-pregnant women.

On the other hand, where the diluents prepared in Examples 1 to 5 were used respectively, all the cases showed negative results, thus indicating no wrong diagnosis.

Next, using the diluents of Examples 1 to 5 respectively, the latex agglutination reaction was conducted on each urine sample of 200 non-pregnant women and 200 pregnant women. With each diluent, all the urine samples of the non-pregnant women showed negative and all the urine samples of the pregnant women showed positive.

TABLE 7

| Diluent for Test Sample | Comparison of Diluents for Test Samples Tested on Urine Samples of Non-Pregnant Women Urine No. | | | | | | | | | |
|---|---|---|---|---|---|---|---|---|---|---|
| | 1 | 2 | 3 | 4 | 5 | 6 | 7 | 8 | 9 | 10 |
| Diluent G | ± | ± | ± | + | ± | + | ± | ± | + | + |
| Diluent H | ± | ± | ± | + | ± | + | + | ± | + | + |
| Example 1 | − | − | − | − | − | − | − | − | − | − |
| Example 2 | − | − | − | − | − | − | − | − | − | − |
| Example 3 | − | − | − | − | − | − | − | − | − | − |
| Example 4 | − | − | − | − | − | − | − | − | − | − |
| Example 5 | − | − | − | − | − | − | − | − | − | − |

TEST EXAMPLE 9

Two drops (about 50 μl) of a urine sample were dropped onto a cleaned glass plate and 1 drop (about 25 μl) of a 0.1 M glycine buffer of pH 8.2 containing 0.1% sodium azide was added and mixed. One drop (about 25 μl) of the diagnostic agent for checking pregnancy containing the anti-HCG antibody sensitized latex particles obtained in Example 17 (2) was added thereto and shaken for 3 minutes, after which the mixture was assessed for the occurrence of the agglutination.

When the latex agglutination reaction was conducted on each urine sample of 200 non-pregnant women and 200 women clinically diagnosed as pregnant, all the urine samples of the non-pregnant women showed negative and all the urine samples of the pregnant women showed positive.

TEST EXAMPLE 10

Two drops (about 50 μl) of a urine sample were dropped onto a cleaned glass plate and two drops (about 50 μl) of the diagnostic agent for checking pregnancy containing the anti-HCG antibody sensitized latex particles obtained in Example 18 were added thereto and shaken for 3 minutes, after which the mixture was assessed for the occurrence of the agglutination.

When the latex agglutination reaction was conducted on each urine sample of 200 non-pregnant women and 200 women clinically diagnosed as pregnant, all the urine samples of the non-pregnant women showed negative and all the samples of the pregnant women showed positive.

TEST EXAMPLE 11

Two drops (about 50 μl) of a urine sample were dropped onto a cleaned glass plate and one drop (about 25 μl) of the diluent for a test sample obtained in Example 10 was added and mixed, after which one drop (about 25 μl) of a latex reagent obtained by dispersing the anti-HCG sensitized latex particles obtained in Example 17 (1) in a 0.1 M glycine buffer of pH 7.8 at a concentration of 1% and shaken for 3 minutes. The mixture was then examined for the occurrence of the agglutination.

When the latex agglutination reaction was conducted on each urine sample of 200 non-pregnant women and 200 women clinically diagnosed as pregnant, all the urine samples of the non-pregnant women showed negative and all the samples of the pregnant women showed positive.

What is claimed is:

1. In an immunoassay comprising incubating a test sample with particles sensitized with an antigen or antibody and observing any resulting agglutination, the improvement wherein the reaction is conducted in the presence of one or more members selected from the group consisting of a compound of the formula

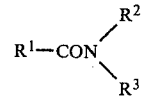

wherein $R^1$ is a hydrogen atom, a lower alkyl group or an amino group which may be substituted with a lower alkyl group and $R^2$ and $R^3$ are each a hydrogen atom or a lower alkyl group, and a di-lower alkyl sulfoxide.

2. A method according to claim 1, wherein the concentration of said member is about 1 to 13% relative to the whole reaction system.

3. A method according to claim 2, wherein the concentration of said member is about 1 to 7.

4. A diluent for a test sample in an immunoassay which involves incubating the test sample together with latex particles sensitized with an antigen or antibody and observing any resulting agglutination, said diluent containing about 4% to 52% of one or more members selected from the group consisting of a compound of the formula

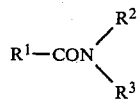

wherein R is a hydrogen atom, a lower alkyl group or an amino group which may be substituted with a lower alkyl group and $R^2$ and $R^3$ are each a hydrogen atom or a lower alkyl group, and a di-lower alkyl sulfoxide, in a buffer liquid having a pH range of about 6 to 9 and an electrolyte concentration of about 0.05 to 0.3 M.

5. A diluent according to claim 4, which contains both urea and N,N-dimethylformamide as said member.

6. A diagnostic reagent which contains about 2% to 52% of one or more members selected from the group consisting of a compound of the formula

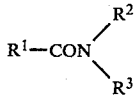

wherein $R^1$ is a hydrogen atom, a lower alkyl group or an amino group which may be substituted with a lower alkyl group and $R^2$ and $R^3$ are each a hydrogen atom or a lower alkyl group, and a di-lower alkyl sulfoxide, and about 0.4% to 1.4% of latex particles sensitized with an antigen or antibody.

7. A diagnostic reagent according to claim 6, wherein the latex particles are of polystyrene.

8. A diagnostic reagent according to claim 6, wherein said member is N,N-dimethylformamide and the latex particles are ones sensitized with anti-C-reactive protein antibody.

* * * * *